(12) United States Patent
Manjeshwar et al.

(10) Patent No.: US 8,472,683 B2
(45) Date of Patent: Jun. 25, 2013

(54) MOTION CORRECTION IN TOMOGRAPHIC IMAGES

(75) Inventors: Ravindra Mohan Manjeshwar, Glenville, NY (US); Kris Filip Johan Jules Thielemans, Putney (GB); Evren Asma, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 846 days.

(21) Appl. No.: 12/550,773

(22) Filed: Aug. 31, 2009

(65) Prior Publication Data

US 2010/0046821 A1    Feb. 25, 2010

Related U.S. Application Data

(63) Continuation-in-part of application No. 12/412,160, filed on Mar. 26, 2009, now Pat. No. 7,920,670, and a continuation-in-part of application No. 12/118,170, filed on May 9, 2008, now Pat. No. 8,098,916.

(51) Int. Cl.
     *G06K 9/00*      (2006.01)

(52) U.S. Cl.
     USPC .......................................... 382/128

(58) Field of Classification Search
     USPC ................................. 382/128–131
     See application file for complete search history.

(56) References Cited

U.S. PATENT DOCUMENTS

| | | | |
|---|---|---|---|
| 6,445,761 B1 * | 9/2002 | Miyazaki et al. | 378/8 |
| 6,449,331 B1 * | 9/2002 | Nutt et al. | 378/19 |
| 6,452,969 B1 | 9/2002 | Yim | |
| 2004/0260176 A1 * | 12/2004 | Wollenweber et al. | 600/427 |
| 2005/0123183 A1 | 6/2005 | Scheleyer et al. | |
| 2005/0129295 A1 * | 6/2005 | Shanmugam et al. | 382/131 |
| 2006/0093089 A1 * | 5/2006 | Vertatschitsch et al. | 378/65 |
| 2006/0178575 A1 * | 8/2006 | Piacsek et al. | 600/413 |
| 2006/0239585 A1 | 10/2006 | Valadez et al. | |
| 2007/0081704 A1 * | 4/2007 | Pan et al. | 382/128 |
| 2007/0232903 A1 | 10/2007 | Hamill | |
| 2008/0095414 A1 | 4/2008 | Desh et al. | |
| 2008/0273780 A1 * | 11/2008 | Kohlmyer et al. | 382/131 |

FOREIGN PATENT DOCUMENTS

| | | |
|---|---|---|
| WO | 2007/100955 A2 | 9/2007 |
| WO | 2008127368 A2 | 10/2008 |

OTHER PUBLICATIONS

Alessio et al "Consistency Driven Respiratory Phase Alignment and Motion Compensation in PET/CT" Nuclear Science Symposium 2007 IEEE, vol. 4, pp. 3115-3119 Oct. 2007.*
M. Irani and S. Peleg; "Super Resolution From Image Sequences"; ICPR, 2:115-120, Jun. 1990.
Vines et al.; "Quantitative PET Comparing Gated with Nongated Acquisitions Using a NEMA Phantom with Respiratory-Simulated Motion"; Journal of Nuclear Medicine Technology • vol. 35 • No. 4 • Dec. 2007; pp. 246-251.
Paul Kinahan, Adam Alessio, Scott Wollenweber, Lydia Ng, Thomas Lewellen, Michelle Wanner, Steve Kohlmyer and Lawrence MacDonald; Abstract : "Motion-free PET: Compensating for patient respiration in whole-body PET/CT imaging"; J Nucl Med. 2007; 48 (Supplement 2):197P; 2 Pages.

\* cited by examiner

*Primary Examiner* — Jingge Wu
(74) *Attorney, Agent, or Firm* — Marie-Claire B. Maple

(57) ABSTRACT

An imaging method comprises reconstructing gated emission tomography images for a region of interest, adjusting a mismatch between the gated emission tomography images and a computed tomography image of the region of interest, registering the gated emission tomography images, and combining the registered gated emission tomography images to generate motion corrected images.

28 Claims, 7 Drawing Sheets

MOTION CORRECTION IN TOMOGRAPHIC IMAGES

CROSS-REFERENCE TO RELATED APPLICATIONS

This application is a continuation-in-part of co-owned, co-pending U.S. patent application Ser. No. 12/118,170 entitled "SYSTEM AND METHOD FOR IMAGE-BASED ATTENUATION CORRECTION OF PET/SPECT IMAGES," filed May 9, 2008, and co-owned, co-pending U.S. patent application Ser. No. 12/412,160 entitled "KEYHOLE COMPUTED TOMOGRAPHY," filed Mar. 26, 2009, which are herein incorporated by reference in their entirety.

BACKGROUND

The invention relates generally to tomographic imaging and, more particularly, to methods and systems for motion correction at a local level for use in tomographic imaging.

Tomographic imaging has become an integral part of healthcare services. Examples of tomographic imaging include positron emission tomography (PET) imaging, single photon emission computed tomography (SPECT) imaging, x-ray computed tomography (CT) imaging, and magnetic resonance imaging (MRI). In CT imaging, x-rays are propagated through the body and are detected on the other side of the body. The x-rays are attenuated to different degrees depending on encountered bodily structures, resulting in an image showing the structural features of the body. But, CT imaging is not particularly sensitive to biological processes and functions.

On the other hand, PET imaging produces images of various biological processes and functions. In PET imaging, a solution including a tracer is injected into a subject or patient to be scanned. The tracer is a pharmaceutical compound including a radioisotope with a relatively short half-life, such as $^{18}$F-fluoro-2-deoxyglucose (FDG), which is a type of sugar that includes radioactive fluorine. The tracer can be adapted such that it is attracted to sites such as lesions within the subject where specific biological or biochemical processes occur. The tracer moves to and is typically taken up in one or more organs of the subject in which these biological and biochemical processes occur. For example, cancer cells may metabolize the tracer, allowing the PET scanner to create an image illuminating the cancerous region. When the radioisotope decays, it emits a positron, which travels a short distance before annihilating with an electron. The short distance that is also referred to as the positron range is typically of the order of 1 mm in common subjects. The annihilation produces two high-energy photons propagating in substantially opposite directions.

PET imaging uses a photon detector array arranged around a scanning area, usually in a ring-shaped pattern, in which the subject or at least the part of interest of the subject is arranged. When the detector array detects two photons within a short timing window, a so-called 'coincidence' is recorded. The line connecting the two detectors that received the photons is called the line of response (LOR). The reconstruction of the image is based on the premise that the decayed radioisotope is located somewhere on the LOR. The relatively short positron range may be neglected or may be compensated for in the reconstruction. Each coincidence may be recorded in a list by three entries: two entries representing the two detectors and one entry representing the time of detection. The coincidences in the list may be grouped in one or more sinograms. A sinogram is typically processed using image reconstruction algorithms to obtain volumetric medical images of the subject. However, PET imaging does not generally provide structural details as well as other types of scanners such as CT and MRI scanners.

A PET-CT scanner includes both a CT scanner and a PET scanner installed around a single patient bore. A PET-CT scanner creates a fused image including a PET image spatially registered to a CT image. PET-CT scanners provide the advantage that the functional and biological features shown by the PET scan may be precisely located with respect to the structure illuminated by the CT scan. In a typical PET-CT scan, the patient first undergoes a CT scan, and then the patient undergoes a PET scan before exiting the scanner. After the CT and PET data have been acquired, the PET-CT scanner processes the data and generates a fused PET-CT image.

Patient motion due to respiration is a significant factor in degrading the quantitative integrity of PET images. Respiratory motion results in contrast dilution of lesions from motion blurring. A second factor that can affect quantification is the inaccurate attenuation correction resulting from motion between the PET and CT acquisitions. Respiratory-gated acquisition of PET and CT images can reduce motion blur. In a respiratory-gated acquisition, the data is partitioned during each respiratory cycle to produce independent images for each partition or gate. Each of these images have reduced motion blur compared to the un-gated image. However, the reduction in blur comes at the expense of increased image noise since each gate has fewer counts than the un-gated image.

Registration of the independent gate images followed by their summation is a method for reducing motion blur without increasing image noise. However, whole body image registration has proven to be challenging to work consistently. It would therefore be desirable to enhance quantitative accuracy in tomographic imaging by providing motion correction in local regions of interest.

BRIEF DESCRIPTION

In accordance with one embodiment disclosed herein, an imaging method comprises reconstructing gated emission tomography images for a region of interest, adjusting a mismatch between the gated emission tomography images and a computed tomography image of the region of interest, registering the gated emission tomography images, and combining the registered gated emission tomography images to generate motion corrected images.

In accordance with another embodiment disclosed herein, an imaging method comprises acquiring computed tomography and emission tomography images, identifying a region of interest for quantification, reconstructing gated emission tomography images for the region of interest adjusting a mismatch between the gated emission tomography images and a computed tomography image of the region of interest, applying an attenuation mismatch correction to the gated emission tomography images, registering the gated emission tomography images, and combining the registered gated emission tomography images to generate motion corrected images.

In accordance with another embodiment disclosed herein, an imaging system comprises at least one receiver to acquire computed tomography and emission tomography images and a processing system to reconstruct gated emission tomography images for a region of interest, adjust a mismatch between the gated emission tomography images and a computed tomography image of the region of interest, apply an attenuation mismatch correction to the gated emission tomography images, register the gated emission tomography images, and combine the registered gated emission tomography images to generate motion corrected images.

DRAWINGS

These and other features, aspects, and advantages of the present invention will become better understood when the following detailed description is read with reference to the accompanying drawings in which like characters represent like parts throughout the drawings, wherein.

Figure 4:
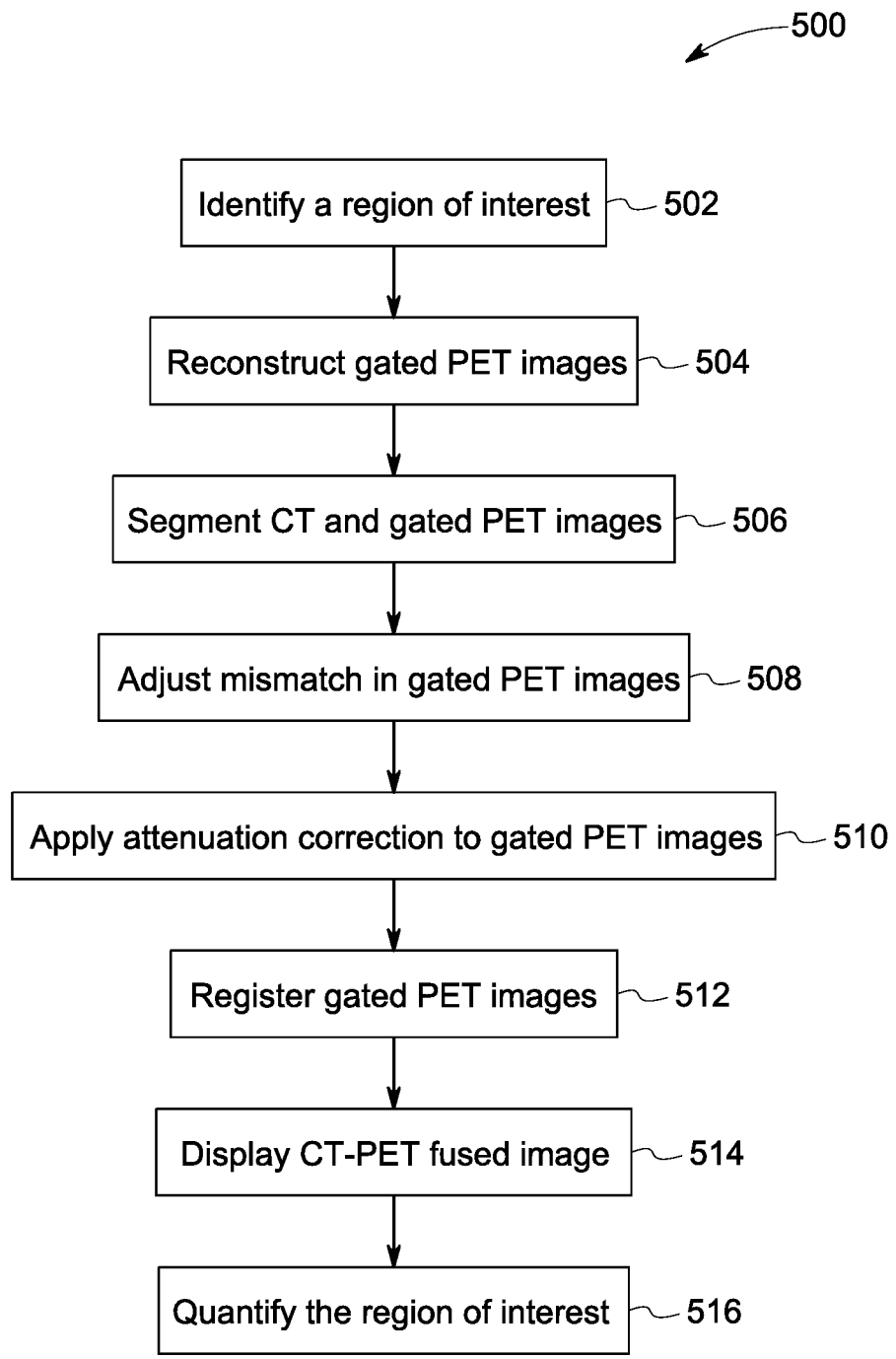

FIG. 4 a flow chart of a method for providing motion correction in accordance with aspects disclosed herein.

Figure 5:
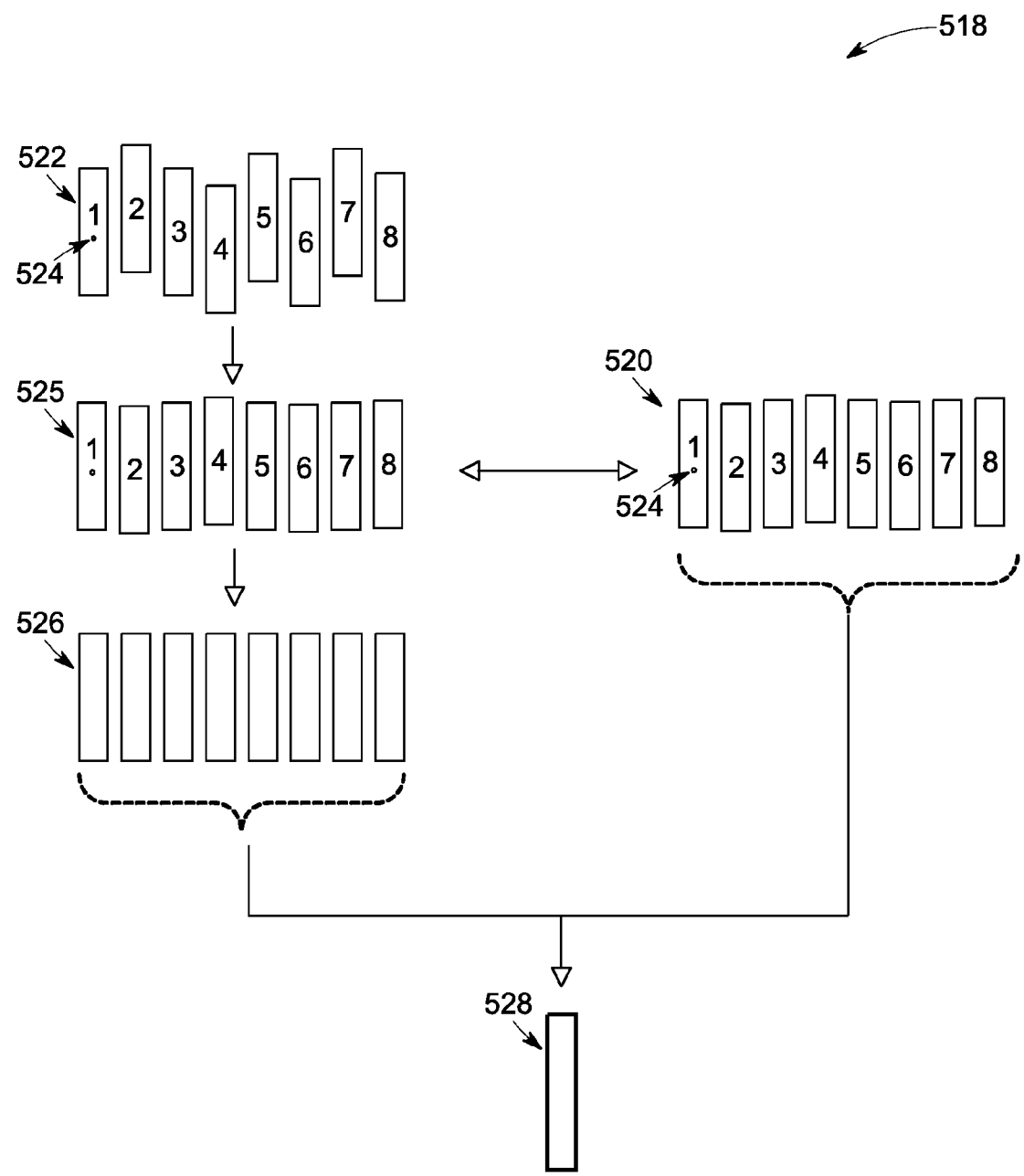

FIG. 5 illustrates an embodiment of mismatch adjustment process in accordance with aspects disclosed herein.

Figure 6:
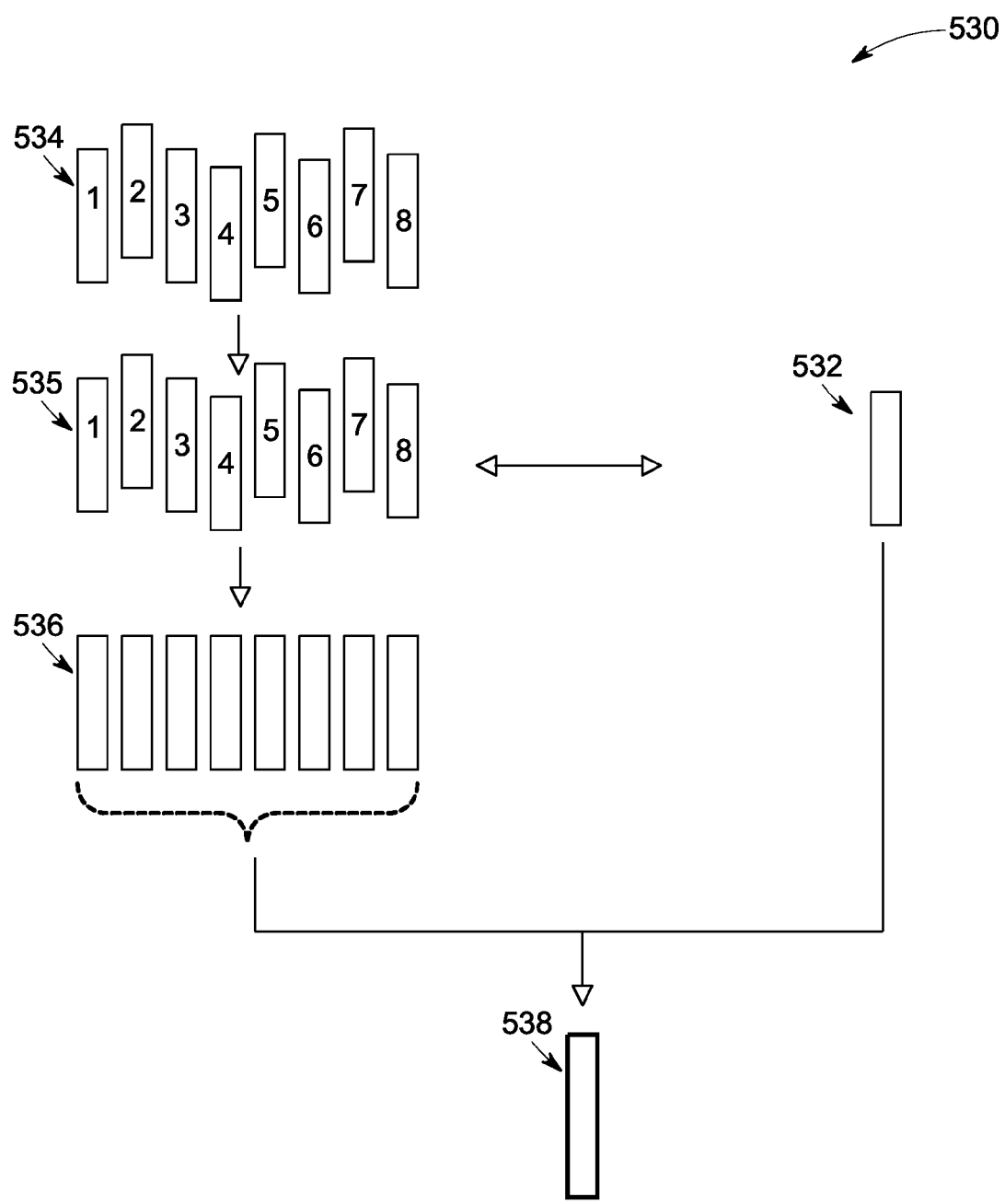

FIG. 6 illustrates another embodiment of mismatch adjustment process in accordance with aspects disclosed herein.

Figure 7:
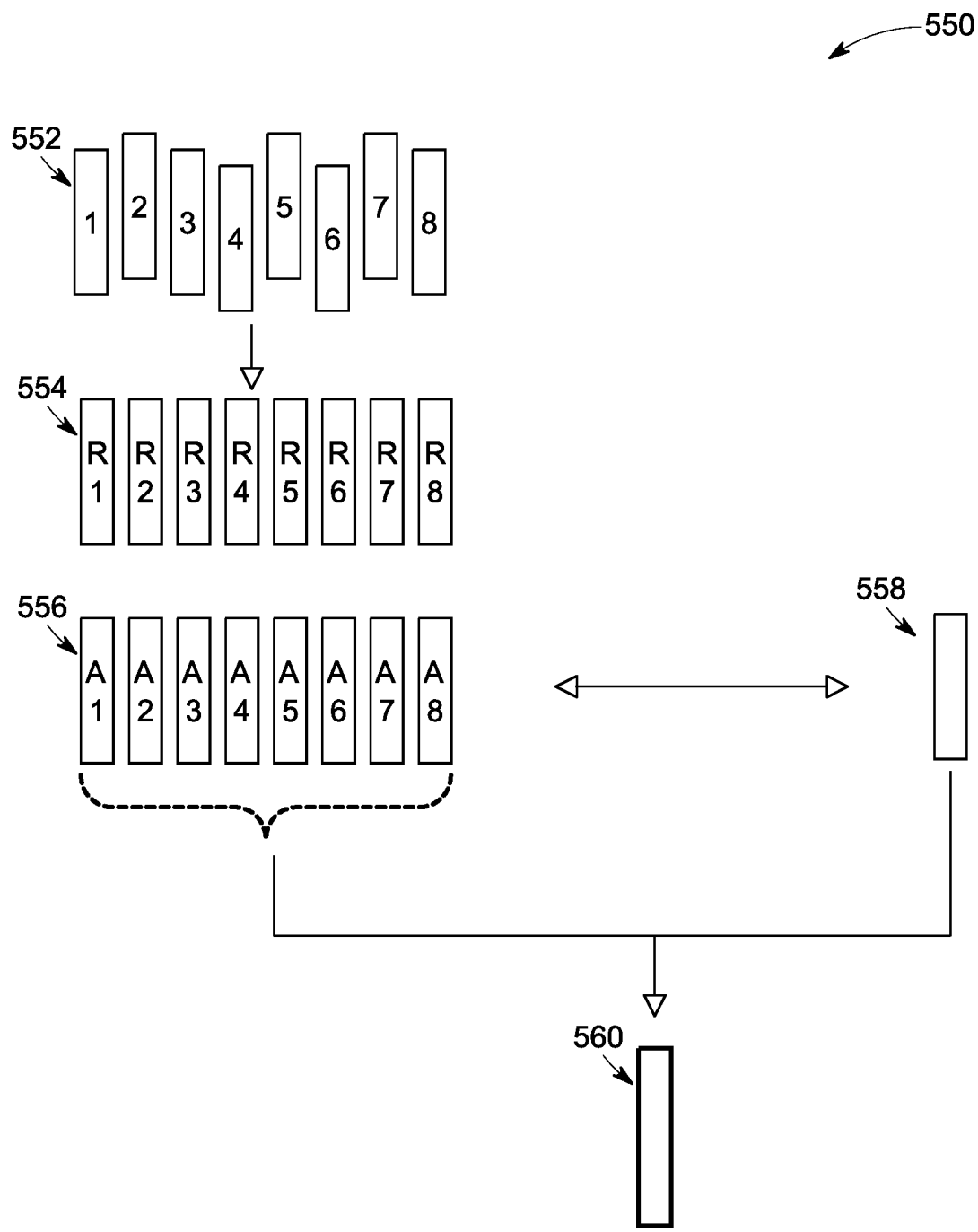

FIG. 7 illustrates another embodiment of mismatch adjustment process in accordance with aspects disclosed herein.

DETAILED DESCRIPTION

Embodiments disclosed herein include an imaging method for providing motion correction in tomographic imaging. The method initially reconstructs respiratory-gated PET and CT images for a region of interest. Patient motion during PET scanning leads to a mismatch in PET and CT images. This mismatch is adjusted between corresponding gated PET and CT images. The mismatch adjustment is performed in PET images to correct motion in the region of interest. An attenuation mismatch correction is then applied to the gated PET images. The gated PET images are then registered. The resulting image is therefore a local motion corrected image. As used herein, singular forms such as "a," "an," and "the" include plural referents unless the context clearly dictates otherwise.

Figure 1:
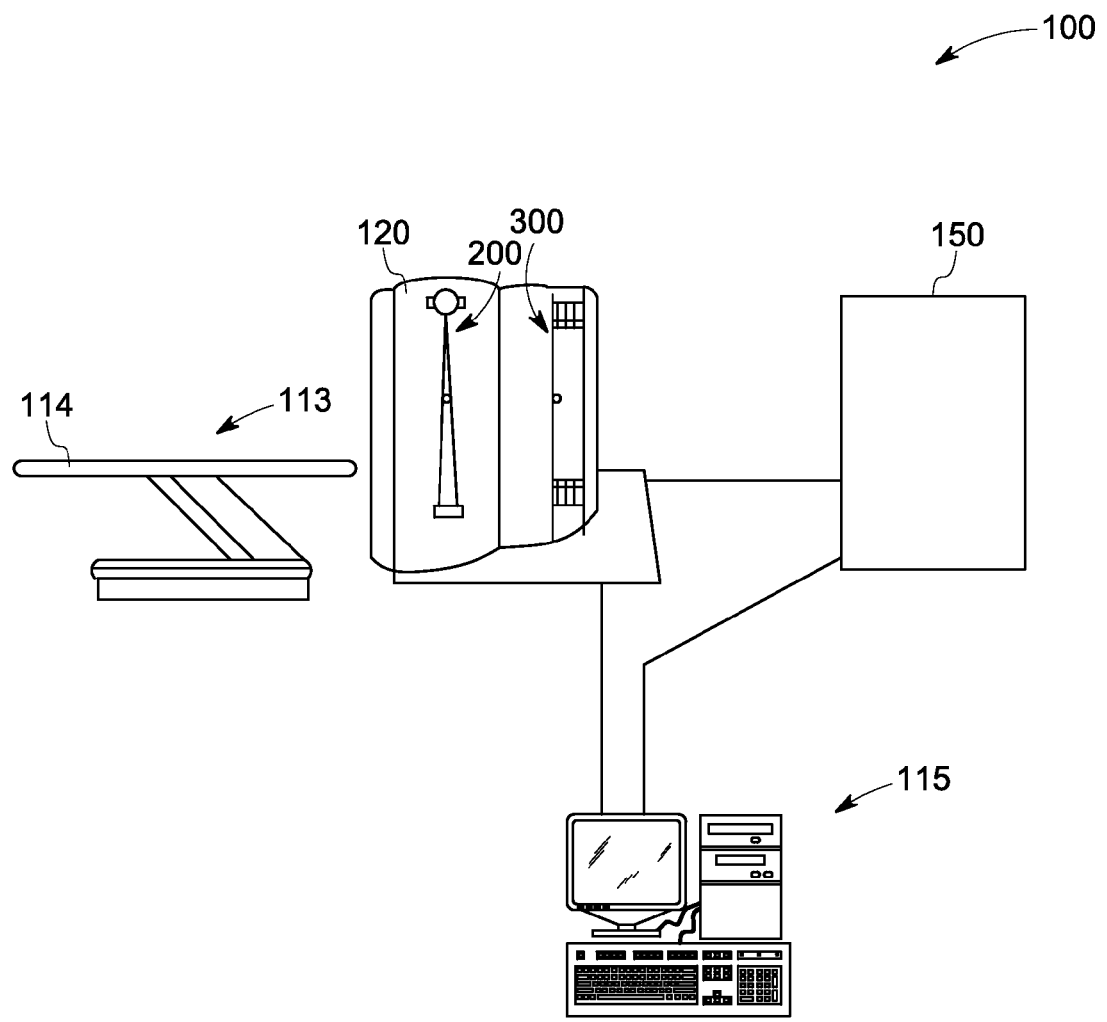
FIG. 1 is a schematic illustration of a PET-CT imaging system.

FIG. 1 illustrates an exemplary embodiment of a PET-CT scanner 100. The PET-CT scanner 100 may include a CT system 200 and a PET system 300 mounted around a bore in a housing 120. The PET-CT scanner 100 may also include a patient table 113, a table bed 114, a processing unit 150, and a control station 115. A patient table controller (not shown) may move the table bed 114 into the bore in response to commands received from the control station 115. The control station 115 may include a display and one or more input devices such as a keyboard, a mouse, or other similar input/controller device. Through the keyboard and associated input devices, the operator may control the operation of the PET-CT scanner 100 and the display of the resulting image on the display.

The processing unit 150 may include one or more processors, one or more memories, and other associated electronics for image processing. The processing unit 150 may process the data acquired by the CT system 200 and the PET system 300 under control of an operator operating the control station 115.

Figure 2:
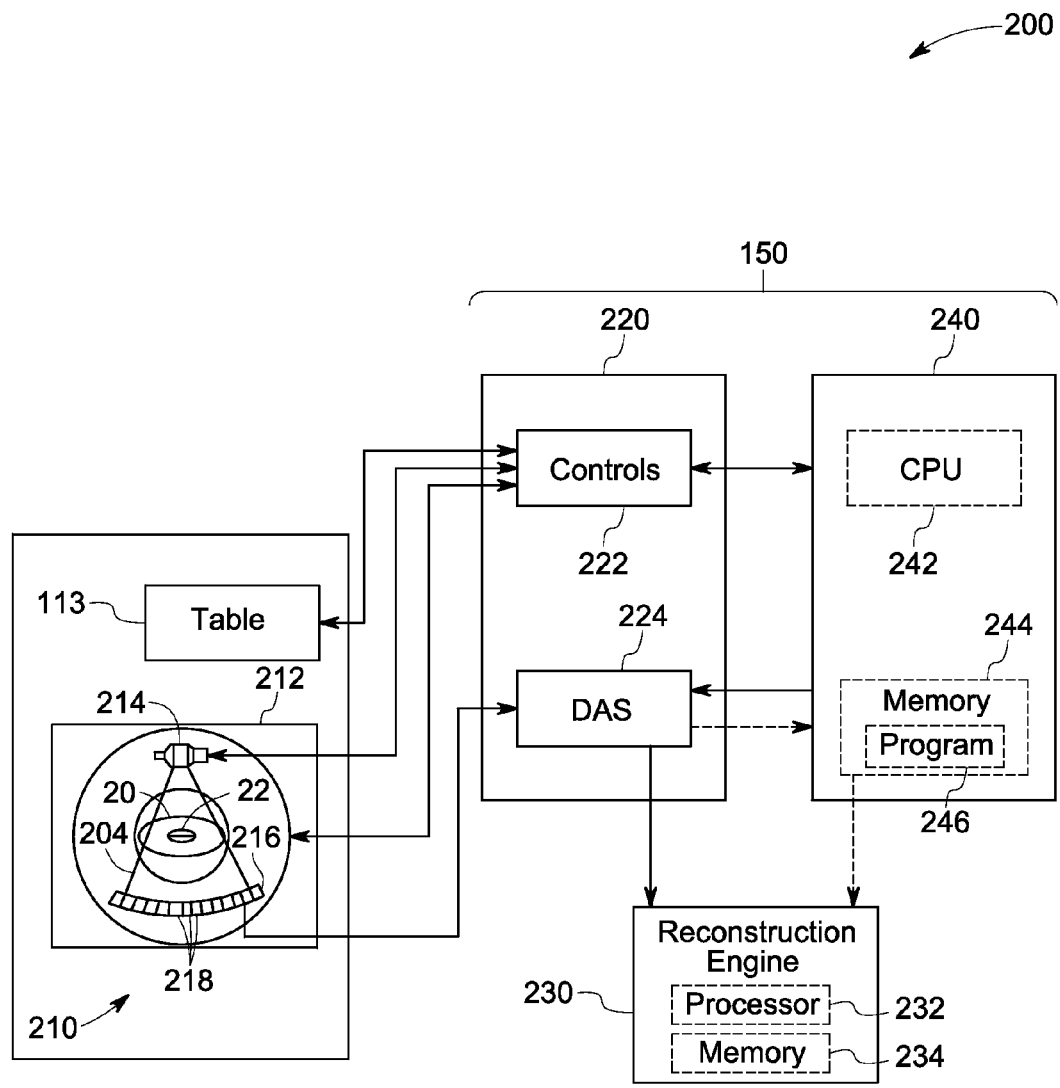
FIG. 2 illustrates an embodiment of CT system architecture.

FIG. 2 depicts major components of the CT system 200 of the PET-CT system 100 according to an exemplary embodiment of the present invention. The components of the CT system 200 may be housed both in the housing 120 supporting the CT detector 200 and in the processing unit 150 shown in FIG. 1. The CT system 200 conducts X-ray tomographic imaging by illuminating a subject 20 with an x-ray beam 204 substantially transverse to an axis through the subject 20. The axis may generally be centered on an object 22 of interest, such as an organ or other tissue structure. The subject 20 may be located on the table bed 114 (as shown in FIG. 1) that translates along the direction of the axis, thereby enabling illumination of a volumetric portion of the subject 20 by the x-ray beam 204.

The CT system 200 may include a source-detector assembly, which in an exemplary embodiment may comprise a gantry 212 rotatable about the axis. An x-ray source 214, such as an x-ray tube, may be mounted on the gantry 212 and may rotate with rotation of the gantry 212. The x-ray source 214, which may comprise a collimating element (not shown), may project the beam 204 of x-rays toward a detector array 216 disposed opposite the source 214 relative to the gantry 212.

The detector array 216 may include numerous individual detector elements 218. Detector elements 218 may together provide information regarding the internal structures of the subject 20, such as the object 22. In one embodiment, each detector element 218 may generate an electrical signal indicating the intensity of a portion of the x-ray beam 204 impinging thereupon.

The signals from detector elements 218 may indicate a degree of attenuation of the beam 204 as the x-rays traverse the material or substance of the subject 20. In one embodiment, the source 214 may be rotated around the subject 20 to execute a scan operation whereby the CT system 200 acquires x-ray data. In another embodiment, the gantry 212, with source 214 attached to a side portion thereof, may rotate about the axis of the subject 20 to acquire x-ray data from numerous different illumination angles or "view angles."

The rotation operation for the source 214 may be controlled by a control/interface system 220. The control/interface system 220 may include a server computer residing in the processing unit 150 and the operator may interact with the control/interface system 220 by means of the control station 115 and/or other input devices. The control/interface system 220 may provide control for positioning of the gantry 212 relative to the subject 20, such as controlling speed of rotation about the axis and control of relative positions of the table 113 and the gantry 212. A controls section 222 may also provide control over x-ray generation (power and timing) of the source 214. The control/interface system 220 may also include a data acquisition system (DAS) 224 that samples the detector signals generated from the detector elements 218 and converts the sampled signals into digital data for further processing.

A reconstruction engine 230, that may also be housed in the processing unit 150, may receive the sampled and digitized data (sometimes referred to as "projection data") from the DAS 224 and may perform image reconstruction to generate CT images. In one embodiment, the reconstruction engine 230 may include a separate processor 232 and/or memory 234. Various algorithms may be utilized for reconstructing a CT image from projection data comprising a plurality of projection views. Generally, the CT image may be generated in a format compatible with the DICOM (Digital Imaging and Communications in Medicine) standard. The DICOM standard specifies the network protocol by which two DICOM-compatible systems communicate.

In one embodiment, the reconstruction engine 230 may send the reconstructed CT image to, for example, a system management computer 240, which system management computer 240 may also reside in the processing unit 150, for storage or further processing. The computer 240 may include a CPU (a processor) 242 and/or at least one memory 244.

Figure 3:
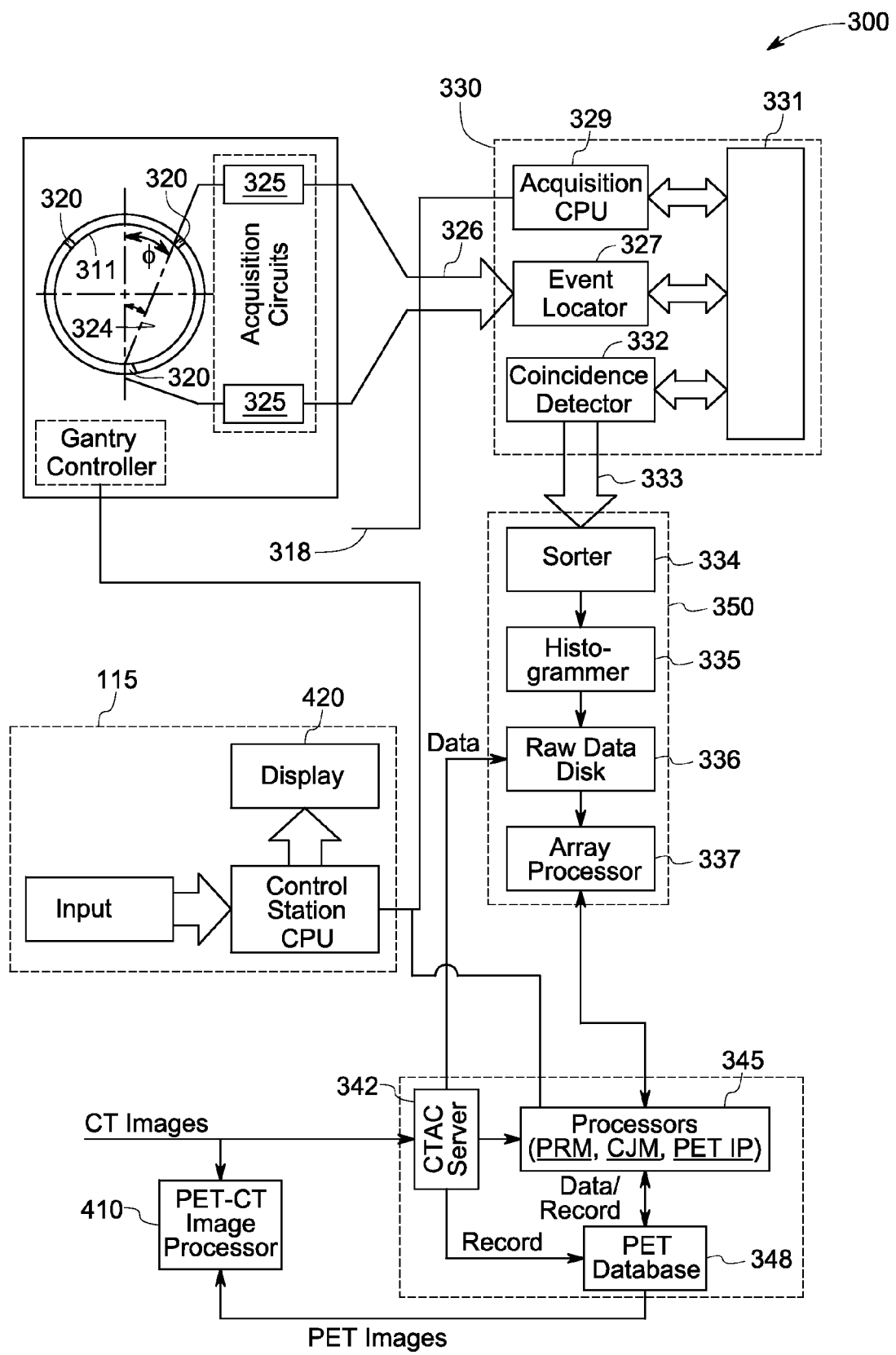
FIG. 3 illustrates an embodiment of PET system architecture.

FIG. 3 illustrates an embodiment of the PET system 300 of the PET-CT imaging system. The PET system 300 may include detector ring assembly 311 disposed about the patient bore. The detector ring assembly 311 may include multiple detector rings that are spaced along the central axis to form a cylindrical detector ring assembly. Each detector ring of the detector ring assembly 311 may be formed of detector modules 320. Each detector module 320 may include an array (e.g., a 6×6 array) of individual detector crystals that may be formed of bismuth germanate (BGO), for example. Other various detector crystals or materials may also be provided. The detector crystals may detect gamma rays emitted from the patient and in response produce photons. In one embodiment, the array of detector crystals may be positioned in front of four photomultiplier tubes (PMTs). The PMTs may produce analog signals when a scintillation event occurs at one of the detector crystals, e.g., when a gamma ray emitted from the patient is received by one of the detector crystals. A set of acquisition circuits 325 may be mounted within the housing 120 (shown in FIG. 1) to receive these signals and produce digital signals indicating the event coordinates (e.g., the location of the detected gamma ray) and the total energy of the gamma ray. These may be sent through a cable 326 to an event locator circuit 327. In another embodiment, each acquisition circuit 325 may also produce an event detection pulse (EDP), which indicates the time the scintillation event took place.

The event locator circuits 327 may form part of a data acquisition processor 330, which periodically samples the signals produced by the acquisition circuits 325. The processor 330 may have an acquisition CPU 329, which controls communications on the local area network 318 and a backplane bus 331. The event locator circuits 327 may assemble the information regarding each valid event into a set of digital numbers that indicate precisely when the event took place and the position of the detector crystal, which detected the event. This event data packet may be conveyed to a coincidence detector 332, which is also part of the data acquisition processor 330.

The coincidence detector 332 may accept the event data packets from the event locator circuits 327 and may determine whether any two of them are in coincidence. In this example, coincidence may be determined by a number of factors. First, the time markers in each event data packet may be required to be within a certain time period of each other, e.g., 12.5 nanoseconds. Second, the locations indicated by the two event data packets may be required to lie on a straight line which passes through the field of view (FOV) in the patient bore. For a detailed description of the coincidence detector 332, reference is made to U.S. Pat. No. 5,241,181 entitled "Coincidence Detector For A PET Scanner," which is hereby incorporated by reference in its entirety. Coincidence event pairs may be located and recorded as a coincidence data packet that is conveyed through a link 333 to a storage subsystem 350. In the storage subsystem 350, a sorter 334 may use a lookup table to sort the coincidence events in a 3D projection plane format. For a detailed description of the sorter 334, reference is made to U.S. Pat. No. 5,272,343 entitled "Sorter For Coincidence timing Calibration In A PET Scanner," which is hereby incorporated by reference in its entirety.

The detected events may be stored in a dynamic histogram memory (histogrammer 335) where the events are ordered by radius and projection angles and other parameters. For example, in Time-of-Flight (TOF) PET scanners, the difference in arrival time of the two photons may also be recorded. In addition, the information on the energy of the photons may also be used. The PET data for a particular frame may be written to a raw data disk 336. TOF PET imaging enables time-difference measurement, e.g., determines the amount of time between the recording of one event by one of the detectors and the recording of the other event by the other detector. Therefore, if an event occurs at the midpoint between these two detectors, the difference in time would be zero. If the event occurs closer to one detector, there will be a delay before the other detector sees it. Thus, TOF makes it possible for a point of origination of annihilation to be more accurately predicted, which leads to more accurate imaging. Ultimately, improved event localization reduces noise in image data, resulting in higher image quality, shorter imaging times, and lower dose to the patient.

The PET system 300, as shown in FIG. 3, may include one or more additional processors 345 such as, for example, a prospective reconstruction manager (PRM), a compute job manager (CJM), and a PET image processor (PET IP). The processors 345 may interact with an array processor 337 in the storage subsystem 350 to process the projection plane format PET data into attenuation corrected PET images.

The PET system 300 may also include a computed tomography attenuation correction (CTAC) server 342. The CTAC server 342 may execute an independent process that runs in the processing unit 150. The CTAC process may receive CT image data from the CT system 200 and convert that CT image data into CTAC data. For example, the CTAC process may receive a request from the CT system and perform a bi-linear or other algorithm to convert the data from CT image units (Hu) to a PET 511 keV attenuation coefficient ($cm^{-1}$), which produces the CTAC correction for PET data from the CT images. Once the CT images are converted to CTAC data, the CTAC server 342 may write the CTAC data to the raw data disk 336 in the storage subsystem 350. At the same time, a record may be transmitted to the PET database 348 to create a data link (CTAC record) to the CTAC data.

The PET system 300 may also include a PET-CT image processor 410 for receiving CT images and PET images. The CT images and the PET images may be spatially registered to each other because the patient undergoes both scans while remaining in the same position on the table bed 114. Registration may be achieved by detecting and estimating patient movement. The PET-CT image processor 410 generates a fused PET-CT image using the input CT and PET images.

It should be appreciated that the arrangement depicted in FIGS. 1-3 is exemplary. For instance, the PET-CT scanner 100 may include different configurations or number of processors, memories, and/or other hardware, to perform various additional functions, and these components may be located at other locations such as the control station 115, or at another server or processing unit. It should also be appreciated that the PET-CT system 100 may be further configured or customized to suit various scanning needs.

FIG. 4 illustrates a flow chart of an embodiment of an imaging method 500 for providing motion correction in accordance with the present invention. The method 500 provides motion correction in local regions of interest and is employed with a PET-CT system, which is described in reference to FIGS. 1-3. Initially, gated PET and gated or un-gated CT data are acquired by the PET and CT systems, respectively. In one embodiment, gating techniques such as respiratory gating or cardiac gating can be used. A region of interest for quantification is identified at block 502. The region of interest can be, for example, a lesion or a portion of a lesion. The region of interest can be identified from a multi-planar display of the un-gated, attenuation corrected PET image. Alternately, the region of interest may be identified by an automatic algorithm running on CT, PET, or PET-CT images.

High resolution gated PET images of the region of interest are reconstructed using keyhole image reconstruction at block 504. The procedure for keyhole image reconstruction is described in detail in a co-owned, co-pending U.S. patent application Ser. No. 12/412,160 entitled "KEYHOLE COMPUTED TOMOGRAPHY," filed Mar. 26, 2009, which is hereby incorporated by reference in its entirety. This keyhole image reconstruction technique is employed to reconstruct gated PET images.

The region of interest is then segmented in the each of the gated PET images and CT images at block 506. Automatic, semi-automatic, or manual delineation techniques can be used for segmenting the region of interest.

Patient motion leads to mismatch or misalignment between PET and CT, leading to inaccurate images when PET and CT data are fused. The CT images and gated PET are compared and a mismatch between corresponding gated PET images and CT images is computed. In one embodiment, the mismatch is adjusted in the gated PET images by comparing them with corresponding CT images at block 508. A reference feature of the region of interest is selected in CT and gated PET images. The mismatch in the gated PET images is adjusted by aligning the gated CT images to the gated PET images based on the reference feature. The feature can be a center of mass of the region of interest or any location on the region of interest. The adjustment of gated PET images corrects misalignment between CT and PET data due to patient motion. Specifically, motion in a region of interest is corrected.

An attenuation mismatch correction is then applied to the gated PET images at block 510. One procedure for applying attenuation correction is described in detail in a co-owned, co-pending U.S. patent application Ser. No. 12/118,170 entitled "SYSTEM AND METHOD FOR IMAGE-BASED ATTENUATION CORRECTION OF PET/SPECT IMAGES," filed May 9, 2008, which is hereby incorporated by reference in its entirety. An alternative procedure consists of re-reconstructing the gated PET data using the keyhole image reconstruction method, where now the aligned CT images are used for attenuation correction.

The gated PET images are then registered and combined at block 512. Several registration techniques can be applied. In one embodiment, the gated PET images are registered to a reference gate through rigid or non-rigid registration and are summed together. In another embodiment, images are registered by aligning centers-of-mass of the gated PET images and then summed. In another embodiment, weight factors such as a weighted sum is used where the weights are a function of the data and/or registration quality. For example, if the gates have different durations, the gates with longer duration should receive a higher weight in the same than the gates with lower duration. Similarly, if registration quality is low, the weight should be low as well. As an example, if segmentation is used for aligning the region of interest, the similarity of the aligned segmented regions, as for example measured by the Jaccard index or the Dice coefficient, can be used to give a confidence metric in the registration. Other registration methods attempt to maximize a similarity metric, and the final value of such metric can be used to determine the weights.

In another embodiment, the gated images are registered and combined at block 512 where the registered images are combined using super-resolution algorithms instead of summation of weighted summation. The super-resolution combination of the low resolution registered images result in a single high-resolution image [for example, M. Irani and S. Peleg. 1991, "Super Resolution From Image Sequences" ICPR, 2:115-120, June 1990]. The super-resolution algorithms can either be frequency domain or spatial domain algorithms.

In another embodiment, motion vectors from the registration are used in motion compensated targeted keyhole reconstruction wherein a single motion corrected image of the region of interest is reconstructed from all the gated data. As in the previous embodiment, weight factors can be used to decrease (or remove) the contribution of gates where the confidence in the registration is low.

The region of interest can be then be displayed at block 514. The display provides a local motion corrected image. Quantification of the region of interest may be performed at block 516. In another embodiment, quantification can be performed in the individual gated images. Statistical parameters such as mean and standard deviation of volumes of region of interest or standardized uptake values (SUV) across respiratory gates may be provided. This will provide feedback on the statistical quality of the final measures. In another embodiment, the quantitative parameters for the individual gated images can be used for outlier gate rejection or for determining weighting factors to be used when combining the motion corrected gated PET images. As an example, if segmentation is used for alignment, the volume of the region of interest is expected to be similar for similar gates. Therefore, if the volume is different in one gate compared to the others, it provides an indication that the segmentation failed, and hence that a low (or zero) weight should be used when combining the aligned gated images.

FIG. 5 illustrates an embodiment mismatch adjustment process 518. Respiratory-gated CT and PET images are reconstructed. As an example, eight gated CT images 520 and eight gated PET images 522 are shown in the figure and are numbered from 1-8. Each of the gated PET images 522 are compared with corresponding gated CT images 520. For example, a first gated PET image is compared with a corresponding first gated CT image. A mismatch in center of masses 524 of first gated PET and CT images is computed. In one embodiment, the mismatch is adjusted by moving the first gated CT image to align the centre of mass of first gated CT image with the center of mass of first gated PET image. Similarly, mismatch between all the corresponding gated CT images and gated PET images is adjusted.

Attenuation mismatch correction is then applied to the mismatch adjusted gated PET images 525. The gated PET images are then registered 526 and fused with gated CT images to provide a motion corrected image 528. The effects of patient motion in a local region of interest are therefore corrected by adjusting the mismatch between corresponding gated CT images and PET images.

In another embodiment 530 as shown in FIG. 6, instead of multiple gated CT images, a single CT image 532 is used. Each of the gated PET images 534 can be compared to the single CT image 532 to adjust the mismatch. Attenuation mismatch correction is then applied to the mismatch adjusted gated PET images 535. The gated PET images are then registered 536 and fused with gated CT images to provide a motion corrected image 538.

Referring to FIG. 7, in another embodiment 550, the gated PET images 552 are registered 554 before applying attenuation mismatch correction. Deformation vectors are obtained using registration and the process of attenuation mismatch correction and PET image alignment is combined in one step at 556. The registered PET gates 552 are referred as R1 to R8 and the attenuation corrected PET gates are referred as A1 to A8. This embodiment is particularly advantageous when a single (un-gated) CT image 558 is available. The original gated PET images can then be aligned to the single CT, and the attenuation mismatch correction 558 can shift the PET images to the CT position, thereby adjusting any mismatch. For example, the attenuation mismatch correction and alignment step can be combined using a keyhole reconstruction process where a single motion corrected image 560 of the region of interest is reconstructed from all the gated data by using the CT position as reference.

The imaging method of the present invention therefore provides a way to locally correct for motion during CT-PET imaging. The method described above is incorporated into the CT-PET system architecture as described in reference to FIGS. 1-3. In one embodiment, the PET-CT image processor 410 (shown FIG. 3) is used as a processing system to perform the method, especially, mismatch adjustment. A display 420 (shown FIG. 3) is used to display the motion corrected PET image or the fused CT-PET image.

While specific reference is made in the present discussion to an X-ray CT imaging system and PET system, it should be appreciated that the present technique is not intended to be limited to these or to any specific type of imaging system or modality. In general, the present technique may be used for providing local motion correction for other tomography imaging combinations such as, for example, CT-SPECT and CT-MRI.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging method, comprising:
   reconstructing gated emission tomography images for a local region of interest;
   comparing the gated emission tomography images to a computed tomography image of the local region of interest to determine if there is a mismatch between the gated emission tomography images and the computed tomography image;
   adjusting the mismatch between the gated emission tomography images and the computed tomography image of the local region of interest common to the computed tomography image and the emission tomography images;
   registering the gated emission tomography images; and
   combining the registered gated emission tomography images to generate motion corrected images.

2. The method of claim 1, wherein adjusting a mismatch comprises adjusting the mismatch in a feature of the region of interest between the computed tomography image and the gated emission tomography images.

3. The method of claim 2, wherein adjusting the mismatch in a feature of the local region of interest, comprises adjusting the mismatch in the feature in the gated emission tomography images.

4. The method of claim 2, wherein the feature comprises a location of the local region of interest comprising a centre of mass.

5. The method of claim 1, further comprising applying an attenuation mismatch correction to the gated emission tomography images.

6. The method of claim 1, wherein the computed tomography image comprises gated computed tomography images.

7. The method of claim 1, further comprises segmenting the computed tomography image and the gated emission tomography images.

8. The method of claim 1, further comprises displaying the local region of interest after registering the gated emission tomography images.

9. The method of claim 1, further comprises generating and displaying a fused computed tomography-emission tomography image.

10. The method of claim 1, wherein the emission tomography images comprise positron emission tomography (PET) images or single photon emission computed tomography (SPECT) images.

11. The method of claim 1, wherein the computed tomography image comprises X-ray computed tomography image.

12. The method of claim 1, wherein reconstructing comprises reconstructing the gated emission tomography images for the local region of interest using keyhole computed tomography.

13. The method of claim 1, wherein weight factors are used in combining the registered gated emission tomography images.

14. The method of claim 1, wherein super-resolution algorithms are used in combining the registered gated emission tomography images.

15. An imaging method, comprising:
    acquiring computed tomography and emission tomography images;
    identifying a local region of interest common to the computed tomography and emission tomography images for quantification;
    reconstructing gated emission tomography images corresponding to the local region of interest;
    adjusting a mismatch between the gated emission tomography images and a computed tomography image of the local region of interest;
    applying an attenuation mismatch correction to the mismatch adjusted gated emission tomography images;
    registering the gated emission tomography images; and
    combining the registered gated emission tomography images to generate motion corrected images.

16. The method of claim 15, wherein adjusting a mismatch comprises adjusting the mismatch in a feature of the local region of interest between the computed tomography image and the gated emission tomography images.

17. The method of claim 16, wherein adjusting the mismatch in a feature of the local region of interest, comprises adjusting the mismatch in the feature in the gated emission tomography images.

18. The method of claim 16, wherein the feature comprises a location of the local region of interest comprising a centre of mass.

19. The method of claim 15, further comprises segmenting the computed tomography image and the gated emission tomography images before adjusting the mismatch and applying the attenuation mismatch correction.

20. The method of claim 15, further comprises displaying the local region of interest after registering the gated emission tomography images.

21. The method of claim 15 further comprises displaying a generating and displaying a fused computed tomography-emission tomography image.

22. The method of claim 15, wherein the emission tomography images comprise positron emission tomography (PET) images or single photon emission computed tomography (SPECT) images.

23. The method of claim 15, wherein the computed tomography image comprises X-ray computed tomography image.

24. The method of claim 15, wherein reconstructing comprises reconstructing the gated emission tomography images for the local region of interest using keyhole computed tomography.

25. The method of claim 15, wherein the computed tomography image comprises gated computed tomography images.

26. The method of claim 15, wherein weight factors are used in combining the registered gated emission tomography images.

27. The method of claim 15, wherein super-resolution algorithms are used in combining the registered gated emission tomography images.

28. An imaging system, comprising:
at least one receiver to acquire computed tomography and emission tomography images; and
a processing system to reconstruct gated emission tomography images for a local region of interest common to the computed tomography and emission tomography images, adjust a mismatch between the gated emission tomography images and a computed tomography image of the local region of interest, apply an attenuation mismatch correction to the mismatch adjusted gated emission tomography images, register the gated emission tomography images, and combine the registered gated emission tomography images to generate motion corrected images.

* * * * *